United States Patent
Fogwill et al.

(10) Patent No.: US 10,006,890 B2
(45) Date of Patent: Jun. 26, 2018

(54) THERMALLY MODULATED VARIABLE RESTRICTOR FOR NORMALIZATION OF DYNAMIC SPLIT RATIOS

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 273 days.

(21) Appl. No.: 14/782,476

(22) PCT Filed: May 15, 2014

(86) PCT No.: PCT/US2014/038027
§ 371 (c)(1),
(2) Date: Oct. 5, 2015

(87) PCT Pub. No.: WO2014/189738
PCT Pub. Date: Nov. 27, 2014

(65) Prior Publication Data
US 2016/0069845 A1 Mar. 10, 2016

Related U.S. Application Data

(60) Provisional application No. 61/826,162, filed on May 22, 2013.

(51) Int. Cl.
*G01N 30/30* (2006.01)
*G01N 30/72* (2006.01)
(Continued)

(52) U.S. Cl.
CPC ............. *G01N 30/30* (2013.01); *G01N 30/16* (2013.01); *G01N 30/7213* (2013.01);
(Continued)

(58) Field of Classification Search
CPC ....... G01N 2030/3038; G01N 30/7213; G01N 2030/324; G01N 30/32; G01N 30/30; B01D 15/161; B01D 15/168
See application file for complete search history.

(56) References Cited

U.S. PATENT DOCUMENTS

| | | |
|---|---|---|
| 4,414,857 A | 11/1983 | Brazhnikov |
| 4,845,985 A | 7/1989 | Berger |

(Continued)

FOREIGN PATENT DOCUMENTS

| | | |
|---|---|---|
| EP | 0356565 A2 | 12/1989 |
| WO | 2006078634 | 7/2006 |

OTHER PUBLICATIONS

International Search Report and Written Opinion in counterpart International Patent Application No. PCT/US14/38027, dated Mar. 27, 2015; 12 pages.

(Continued)

*Primary Examiner* — Paul West
(74) *Attorney, Agent, or Firm* — Schmeiser, Olsen & Watts LLP

(57) ABSTRACT

A chromatography system includes a separation column that separates a sample carried by a compressible mobile phase flow into analytes and a splitter in fluidic communication with the separation column to receive and divide the compressible mobile phase flow into first and second mobile phase streams in accordance with a split ratio. A thermally modulated variable restrictor is coupled between the splitter and a detector. The restrictor receives the first mobile phase stream from the splitter and has a temperature element in (Continued)

thermal communication with the first mobile phase stream to exchange heat therewith. A controller, in communication with the restrictor, dynamically adjusts a temperature setting of the temperature element of the restrictor to adjust the heat exchange between the thermally modulated variable restrictor and the first mobile phase stream in order to keep the split ratio constant throughout a chromatographic run.

36 Claims, 7 Drawing Sheets

(51) Int. Cl.
| | |
|---|---|
| *G01N 30/16* | (2006.01) |
| *G01N 30/84* | (2006.01) |
| *B01D 15/40* | (2006.01) |
| *G01N 30/34* | (2006.01) |
| *B01D 15/16* | (2006.01) |
| *G01N 30/32* | (2006.01) |

(52) U.S. Cl.
CPC ........... *G01N 30/84* (2013.01); *B01D 15/161* (2013.01); *B01D 15/40* (2013.01); *G01N 30/32* (2013.01); *G01N 30/34* (2013.01); *G01N 2030/3038* (2013.01)

(56) References Cited

U.S. PATENT DOCUMENTS

| | | | |
|---|---|---|---|
| 4,962,662 | A | 10/1990 | Berger |
| 4,982,597 | A | 1/1991 | Berger |
| 5,274,903 | A | 1/1994 | Grois et al. |
| 5,336,869 | A | 8/1994 | Kumar |
| 5,340,475 | A | 8/1994 | Cortes et al. |
| 6,183,635 | B1 | 2/2001 | Klee et al. |
| 6,294,088 | B1 | 9/2001 | Allington et al. |
| 6,557,575 | B1 | 5/2003 | Gerhardt et al. |
| 6,865,829 | B2 | 3/2005 | O'Brien et al. |
| 6,878,909 | B2 | 4/2005 | Bergstrom et al. |
| 2004/0237627 | A1 | 12/2004 | Jochum, Jr. |
| 2005/0121392 | A1 | 6/2005 | Hoffman |
| 2006/0054558 | A1 | 3/2006 | Jones et al. |
| 2006/0186029 | A1 | 8/2006 | Granger et al. |
| 2008/0121576 | A1 | 5/2008 | Gerhardt et al. |
| 2008/0302423 | A1 | 12/2008 | Gerhardt et al. |
| 2009/0165873 | A1* | 7/2009 | Chordia ............... G01N 30/84 137/597 |
| 2010/0101411 | A1 | 4/2010 | Tipler |
| 2011/0113866 | A1 | 5/2011 | Finlay |
| 2011/0233299 | A1 | 9/2011 | Berger et al. |
| 2012/0118049 | A1 | 5/2012 | Tipler |
| 2012/0305092 | A1 | 12/2012 | Corso et al. |

OTHER PUBLICATIONS

Berger, T.A. and B.S. Todd, "Packed Column Supercritical Fluid Chromatography of Oligoethers using Pure Carbon Dioxide with Flame Ionization and Ultraviolet Detection", Chromatographia, Dec. 2001, pp. 777-781, vol. 54, No. 11/12.

Berger, T.A., "Simple Correction for Variable Post Column Split Ratios using Pure Carbon Dioxide in Packed Column Supercritical Fluid Chromatography with Independent Pressure and Flow Control", Chromatographia, Dec. 2001, pp. 783-788, vol. 54, No. 11/12.

Berger, T.A. and C. Toney, "Linear Velocity Control in Capillary Supercritical Fluid Chromatography by Restrictor Temperature Programming", Journal of Chromagtography, 1989, pp. 157-167, No. 465.

Pyo, Dongjin, "Programmed Two-stage Flow Controller for Supercritical Fluid Chromatography", Analyst, Jun. 1994, pp. 1315-1318, vol. 119.

Pyo, Dongjin, "Temperature-controlled Restrictor for UV Detection in Capillary Supercritical Fluid Chromatography", Bull. Korean Chem. Soc., 2006, pp. 1429-1432, vol. 27, No. 9.

Greibrokk, et al., "Techniques and Applications in Supercritical Fluid Chromatography", Journal of Chromatography, 1987, pp. 429-441, vol. 394.

Li, Jian Jun and Kevin B. Thurbide, "Dynamic control of split flow in packed column supercritical fluid chromatography using dual resistively heated restrictors", J. Sep. Sci. 2009, pp. 2469-2475, vol. 32.

Li, Jian Jun and Kevin B. Thurbide, "Novel pressure control in supercritical fluid chromatography using a resistively heated restrictor", Can. J. Chem. 2009, pp. 490-495, vol. 87.

Page, et al., "Restrictor plugging in off-line supercritical fluid extraction of environmental samples, Microscopic, chemical and spectroscopic evaluations", Journal of Supercritical Fluids, 1999, pp. 257-270, Elsevier Science Publishers B.V.

Olesik, Susan V. and L.A. Pekay, "A Model for Quantitatively Describing Linear Velocity Programming in Capillary SFC," Chromatographia, Jan. 1990, vol. 29, No. 1/2, Germany, pp. 69-75.

International Search Report & Written Opinion in International Patent Application No. PCT/US14/13153, dated May 5, 2014; 20 pages.

International Search Report & Written Opinion in International Application No. PCT/US14/13985, dated May 16, 2014; 8 pages.

International Preliminary Report on Patentability in International Patent Application No. PCT/US14/13153, dated Sep. 24, 2015; 18 pages.

International Preliminary Report on Patentability in International Patent Application No. PCT/US14/13985, dated Sep. 24, 2015; 7 pages.

Extended Search Report in European patent application No. 14764098.1, dated Sep. 23, 2016; 9 pages.

International Preliminary Report on Patentability in counterpart International Application No. PCT/US14/38027, dated Dec. 3, 2015; 10 pages.

Extended Search Report in counterpart European Patent Application No. 14800388.2, dated Nov. 29, 2016; 10 pages.

Lord, et al. "Tapers and restrictors for capillary electrochromatography and capillary electrochromatography-mass spectrometry," Journal of Chromatography, Apr. 18, 1997, pp. 9-16, vol. 768, No. 1.

Baek, et al. "Wireless induction heating in a microfluidic device for cell lysis," Lab on a Chip, vol. 10, Jan. 2010, pp. 909-917.

Non-Final Office Action in U.S. Appl. No. 14/773,780, dated Aug. 10, 2017; 16 pages.

\* cited by examiner

THERMALLY MODULATED VARIABLE RESTRICTOR FOR NORMALIZATION OF DYNAMIC SPLIT RATIOS

RELATED APPLICATION

This application claims the benefit of and priority to U.S. provisional application No. 61/826,162, filed May 22, 2013, titled "Thermally Modulated Variable Restrictor for Normalization of Dynamic Split Ratios" the entirety of which is incorporated by reference herein.

FIELD OF THE INVENTION

The invention relates to chromatography systems that employ a compressible mobile phase during chromatographic runs, split the compressible mobile phase flow, and control the split ratio using a thermally modulated variable restrictor.

BACKGROUND

Carbon dioxide-based chromatography systems, for example, SFC (supercritical fluid chromatography) systems, employ a compressible mobile phase as a carrier fluid. Separations performed by such chromatography systems require independent control over the mobile phase flow rate and system pressure in order to maintain a constant linear velocity through the separation column For chromatography systems using packed bed, analytical-scale separation columns, a backpressure regulator (BPR) often provides this decoupling of mobile phase flow rate and system pressure.

In addition, a common practice in chromatography systems with analytical-scale separation columns is to split the compressible mobile phase flow. Splitting the compressible mobile phase flow overcomes two system limitations. One is that BPR can contribute significant dead (i.e., extra) volume to the chromatography system, significantly broadening the resulting chromatographic peaks and making detection downstream of the BPR undesirable; splitting provides a path by which to direct a portion of the mobile phase flow towards a detector, a path without the BPR. The second is that detectors, such as mass spectrometers (MS) and flame ionization detectors (FID), among others, are designed to achieve an optimum response within a tight window for the mobile phase flow rate; splitting the compressible mobile phase enables the chromatography system to provide the optimum flow rate consistently to the detector over a wide range of total system flow rates governed by the separation column. Detection downstream of the BPR is further undesirable because the mobile phase has decompressed after the BPR, leaving no appreciable mobile phase density available for transporting the analyte. In this instance, high molecular weight and/or low volatility analytes will precipitate out of the mobile phase without ever reaching the detector.

Typically, the chromatography system achieves this splitting with a fixed restrictor installed in a tee fitting residing in the compressible mobile phase stream. The fixed restrictor routes a portion of the total mobile phase flow rate towards the detector for detection. In addition, the tee fitting routes a majority portion of the mobile phase flow rate to the BPR for maintaining and controlling system pressure.

This fixed restrictor configuration runs into problems, however, when the mobile phase density or composition changes during the course of a separation. Altering the mobile phase density or composition as the separation progresses (gradient separations) are commonly employed techniques for improving the peak capacity of the separation column Because the viscosity of the mobile phase changes with programmed changes to the mobile phase density or composition, the flow rate through the fixed restrictor changes, too. This change in flow rate causes a change in the split ratio (i.e., the ratio of the total mobile phase flow rate delivered by the pump to the minority portion mobile phase flow rate measured at the detector) as the separation progresses (a larger split ratio means a smaller portion of the mobile phase is directed to the detector). Therefore, the split ratio for latter eluting peaks differs from that for earlier eluting peaks. This difference in the split ratio creates a non-linearity, which poses a problem for quantitation of all peaks in the gradient separation. In addition to changes in viscosity, the split ratio changes simply by increasing the BPR pressure (i.e., pressure at the head of the split restrictor). The pump maintains a constant flow rate of the mobile phase across the column as the BPR increases the pressure. The fixed restrictor allows more mobile phase to pass to the detector as pressure increases and, therefore, the split ratio drops (i.e., a larger portion of the analyte is directed to the detector).

SUMMARY

In one aspect, the invention features a chromatography system comprising a separation column separating a sample carried by a compressible mobile phase flow into analytes and a fluidic splitter in fluidic communication with the separation column to receive and divide the compressible mobile phase flow containing the separated sample into first and second mobile phase streams in accordance with a split ratio. A thermally modulated variable restrictor is coupled between the fluidic splitter and a detector. The thermally modulated variable restrictor receives the first mobile phase stream from the fluidic splitter and has a temperature element in thermal communication with the first mobile phase stream to exchange heat therewith. A controller, in communication with the thermally modulated variable restrictor, dynamically adjusts a temperature setting of the temperature element of the thermally modulated variable restrictor to adjust the heat exchange between the thermally modulated variable restrictor and the first mobile phase stream in order to keep the split ratio constant throughout a chromatographic run.

In another aspect, the invention features a method for performing a chromatographic run. The method comprises dividing a compressible mobile phase flow containing a separated sample in accordance with a split ratio whereby a first portion of the divided compressible mobile phase flow moves at a first mass flow rate towards a detector through a thermally modulated variable restrictor and a second portion of the divided compressible mobile phase flow moves at a second mass flow rate to a system pressure regulator. A temperature setting of the thermally modulated variable restrictor is dynamically adjusted to adjust a heat exchange between the thermally modulated variable restrictor and the first portion of the divided compressible mobile phase flow in order to keep the split ratio constant throughout the chromatographic run.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
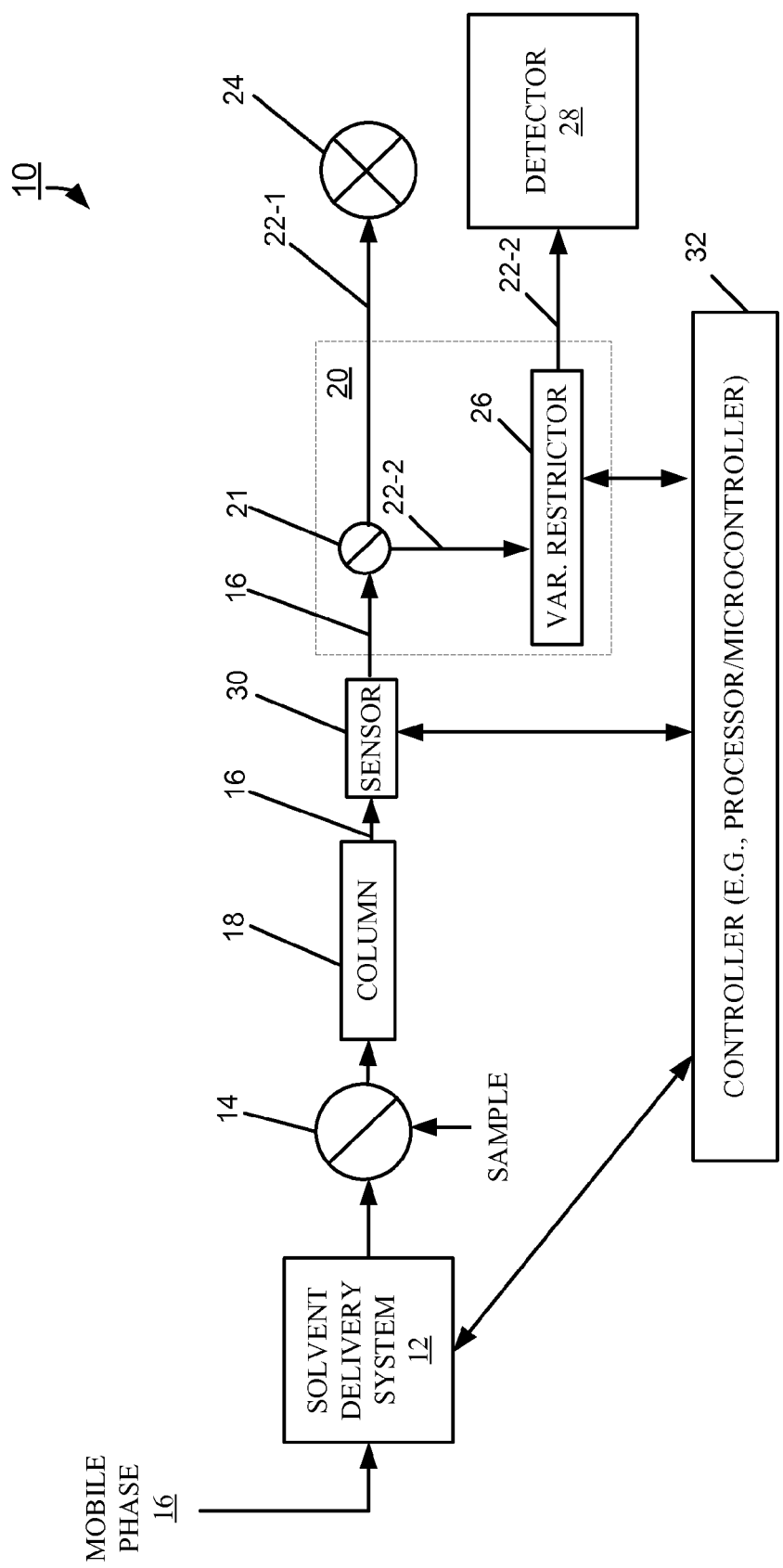
FIG. 1 is a block diagram of an embodiment of a $CO_2$-based chromatography system including a splitter in fluidic communication with a system pressure regulator and a thermally modulated variable restrictor.

Carbon dioxide-based chromatography systems described herein include a fluidic splitter that routes a major portion of a compressible mobile phase flow rate to a system pressure regulator and a minor portion of the compressible mobile phase flow rate to a detector through a thermally modulated variable restrictor in accordance with a target split ratio. Dynamically controlled operation of the thermally modulated variable restrictor, as described herein, normalizes the split ratio throughout the course of a density-programmed gradient separation and/or a composition-programmed gradient separation (i.e., chromatographic run). Normally, density programmed and/or composition-programmed gradients alter the split ratio when a static restrictor performs the split. Installing a thermally modulated variable restrictor instead of a static restrictor allows for the normalization of changes in the split ratio as the gradient separation progresses.

Various embodiments of thermally modulated variable restrictors can be used to dynamically control the split ratio. To avoid premature analyte precipitation, some embodiments of these thermally modulated variable restrictors have shorter decompression distances than those of conventional heated restrictors. The decompression distance corresponds to the length along the restrictor over which the compressible mobile phase can expand from the dense fluid phase to gas. A short decompression distance thus maintains an appreciable mobile phase density through the fluidic channel of the restrictor as long as possible to prevent analyte precipitation and consequential plugging. In brief overview, some of these embodiments of thermally modulated variable restrictors confine the decompression distance to a short region (called the restrictor tip) disposed at the outlet end of a fluidic channel embodied within a restrictor body. Alternatively, conventional heated restrictors can also be used to dynamically control the split ratio, as described herein.

Embodiments of the restrictor body include tubes and microfluidic substrates (or tiles). The restrictor tip has one or more egress openings that are smaller than the internal diameter of the fluidic channel and, thus, restrict the flow of the mobile phase passing through the fluidic channel. Embodiments of the restrictor tip include a short length of straight, small ID tubing, a tapered restrictor, a pinched restrictor, a fritted restrictor, an integral restrictor, or a crimped restrictor (e.g., a restrictor tip crimped onto the end of the heated restrictor body, or a restriction formed by crimping a metal tube that reduces its ID). This restrictor tip can be replaceable or permanently affixed to the restrictor body with the fluidic channel. The outlet of the chromatography column couples directly to the inlet end of the fluidic channel, through which the mobile phase enters the restrictor.

A heating element may be used to heat a subsection of the fluidic channel with the relatively large ID (greater than or equal to 100 µm), where the linear velocity of the mobile phase is relatively low. A slowly moving mobile phase provides sufficient time for an energy transfer from the heating element to the mobile phase. As the heating element heats the mobile phase in the subsection of the fluidic channel, the effective restriction increases. The density of the mobile phase decreases as its temperature rises. This decrease in density causes a volumetric expansion and a significant increase in the linear velocity of the mobile phase. The increase in linear velocity across the restrictor tip causes an increase in restriction in the system. This restriction operates to maintain a minimum density of the mobile phase, preventing the mobile phase in the fluidic channel from evaporating to gas until it reaches the egress opening of the restrictor tip, where decompression occurs. Relatively low temperatures, for example, ranging between 150° C. and 250° C., are capable of producing a restrictive backpressure sufficient to control the flow rate of the mobile phase through the variable restrictor, while maintaining the mobile phase substantially in dense fluid form within the restrictor body until the mobile phase reaches the restrictor tip.

Because the decompression distance of the variable restrictor is relatively short, being substantially limited to the short region of the restrictor tip, the fluidic channel is relatively unsusceptible to plugging. Further, should a replaceable restrictor tip clog or plug, the heated restrictor body of the thermally modulated variable restrictor would remain intact, while only the restrictor tip, typically far less expensive than the heated restrictor body, would need replacing.

Instead of, or in addition to a heating element, other embodiments of thermally modulated variable restrictors can have a cooling element, for example, a Peltier device or other thermoelectric cooling device or liquid $CO_2$, to cool the subsection of the fluidic channel with the relatively large ID. The cooling element can rapidly cool the variable restrictor to its initial temperature, to reduce further the linear velocity through sub-ambient cooling. Alternatively, the cooling element can be used to freeze the $CO_2$ in place and form a plug in the system. Liquid nitrogen, for example, can be used to produce this result. Freezing the $CO_2$ in place can be a useful technique to shut off the flow through the variable restrictor.

FIG. 1 shows an embodiment of a carbon dioxide-based chromatography system 10 for separating a sample into its constituents. The chromatography system 10 includes a solvent delivery system 12 in fluidic communication with a sample injector 14. Fluidically coupled to the solvent delivery system 12 are one or more sources of solvents (not shown) used during the course of a chromatographic run (i.e., a sample separation). The chromatographic run occurs under predetermined pressure conditions, which are either static or programmed dynamic pressure conditions. The solvent delivery system 12 can operate in a constant-pressure mode or in a constant-flow mode. In the constant-pressure mode, the solvent delivery system 12 produces the system pressure in the chromatography system 10 with one or more pumps (not shown) in accordance with, for example, a density program. When in the constant-flow mode, the solvent delivery system 12 provides a set mass flow rate of solvent. This mass flow rate can be programmable.

From these sources of solvent, the solvent delivery system 12 draws a fluid, referred to as a compressible mobile phase 16, and moves this mobile phase 16 to the sample injector 14. Preferably, the solvents include a fluid (e.g., $CO_2$) that is in a gaseous state at ambient/room temperature and atmospheric pressure. When a sample is run with pure $CO_2$, the mobile phase 16 has gained appreciable density (i.e. solvating power) at elevated pressure and/or temperature. In addition to the $CO_2$, the mobile phase can contain a modifier (e.g., methanol) and ternary additives (e.g., pH controllers). The composition of the mobile phase 16 can change over the course of a chromatographic run in accordance with a gradient program.

The sample injector 14 is in fluidic communication with a sample source from which the sample injector 14 acquires a sample (i.e., the material under analysis) and introduces the sample to the mobile phase 16 arriving from the solvent delivery system 12. Examples of samples include complex mixtures of proteins, protein precursors, protein fragments, reaction products, and other compounds, to list but a few.

In addition, the sample injector 14 is in fluidic communication with a separation column 18. The mobile phase 16, which includes the injected sample, passes from the sample injector 14 to and through this separation column 18. The separation column 18 is adapted to separate the various components (or analytes) of the sample from each other at different rates as the mobile passes 16 through, and to elute the analytes (still carried by the mobile phase) from the separation column 18 at different times. Embodiments of the separation column 18 include a variety of sizes (e.g., preparative, semi-preparative, analytical-scale (e.g., 4.6 mm ID), or capillary-scale packed-bed columns or open tubular columns) and a variety of preparations (e.g., in conventional metallic, fused silica, or polymeric tubes, or in metallic, ceramic, silica, glass, or polymeric microfluidic platforms or substrates of various IDs).

In fluidic communication with an outlet end of the separation column 18 is an active fluidic splitter 20, which divides the main mobile phase flow 16 (containing the sample) received from the separation column 18 into first and second mobile phase streams 22-1, 22-2, respectively. The active fluidic splitter 20 includes a tee fitting 21 and a thermally modulated variable restrictor 26. The tee fitting 21 directs the first mobile phase stream 22-1 to a system pressure regulator 24 and the second mobile phase stream 22-2 to the thermally modulated variable restrictor 26. The first mobile phase stream 22-1 comprises a majority portion of the main mobile phase flow 16; the second mobile phase stream 22-2, a minority portion of the main mobile phase flow 16.

The split of the main mobile phase flow 16 into mobile phase streams 22-1, 22-2 is in accordance with a target split ratio. The split ratio can be described in any one of a variety of ways, for example, as the ratio of the mass flow rate of the first mobile phase stream 22-1 to the second mobile phase stream 22-2, or the inverse ratio, or as the ratio of the total mass flow rate of the main mobile phase flow 16 to the mass flow rate of the minority mobile phase stream 22-2, or its inverse ratio. Other manners of defining the split ratio can be used without departing from the principles described herein whereby the split ratio is held constant throughout a chromatographic run. For purposes of illustrating these principles, the following description defines the split ratio as the ratio of the total mass flow rate of the main mobile phase flow 16 to the mass flow rate of the minority mobile phase stream 22-2. For purposes of demonstrating the relative scale of the mass flow rates, this split ratio can often range between 4:1 and 100:1 or greater.

Various embodiments of the active splitter 20 can be adapted for different types of $CO_2$-based chromatography systems, for example, SFC, operating with preparative, semi-preparative, analytical, or capillary-scale packed-bed columns or open tubular columns prepared as previously described. In addition, the active splitter 20 can be employed with FID (Flame Ionization Detector), MS (Mass Spectrometer), or any other detector where the amount of inlet flow may need limiting. Further, this type of active splitter could be utilized in HPLC (High Performance Liquid Chromatography), UPLC (Ultra Performance Liquid Chromatography), SFC, GC (gas chromatography), dense GC, or solvating GC separation schemes.

The system pressure regulator 24 receives the first mobile phase stream 22-1 from an outlet of the tee fitting 21 and uses this mobile phase stream 22-1 to regulate the system pressure of the chromatography system 10. Embodiments of the system pressure regulator 24 include, but are not limited to, a fixed restrictor, a thermally modulated variable restrictor, or a backpressure regulator.

An inlet end of the thermally modulated variable restrictor 26 receives the second mobile phase stream 22-2 from a second outlet of the tee fitting 21. In general, the thermally modulated variable restrictor 26 operates to keep the split ratio constant throughout a chromatographic run. Embodiments of the thermally modulated variable restrictor 26 can be fashioned as one or more sections of tubing or as a channel in a metallic, ceramic, silica, glass, or polymeric microfluidic device. Implementations of the thermally modulated variable restrictor 26 can be made of metal, fused silica, silica, glass, or polymeric tubing or microfluidic devices of various geometries and cross sectional aspect ratios.

Control of the split ratio of the mobile phase rates occurs by controlling the restriction produced by the thermally modulated variable restrictor 26. Such control depends upon the temperature of the second mobile phase stream 22-2 passing through the thermally modulated variable restrictor 26, and control of this temperature is achieved by controlling the heat exchanged between the thermally modulated variable restrictor 26 and the second mobile phase stream 22-2. As illustrated in FIGS. 2-9, each embodiment of the thermally modulated variable restrictor 26 includes a heated region that exchanges heat with the second mobile phase stream 22-2 passing through that region.

In brief overview, as system pressure increases during a density program, the temperature setting of the thermally modulated variable restrictor 26 may be increased or decreased to maintain the same split ratio. Without this control, the split ratio would increase or decrease as the density gradient progresses. Increasing the temperature of the variable restrictor 26, for example, increases the restriction and thereby reduces the split ratio (i.e., to offset an increase in the split ratio caused by an increase in system pressure). Similarly, as the amount of modifier is increased during a composition gradient, the temperature of the thermally modulated variable restrictor is changed to maintain the same split ratio. Without this temperature control of the variable restrictor, and, thus, of the minority mobile phase stream 22-2 flowing therethrough, the split ratio would vary as the density gradient progresses.

The outlet end of the thermally modulated variable restrictor 26 may be coupled to a detector 28. Typically, the tip of the thermally modulated variable restrictor 26 resides within the detector 28 (i.e., heated Flame Ionization Detector (FID) jet or the mass spectrometer ion source). In such embodiments, a transfer line does not couple the thermally modulated variable restrictor 26 to the detector 28. In general, the detector 28 can operate with a low flow rate such as that produced by the thermally modulated variable restrictor 26 upon the second (minority) mobile phase stream 22-2. In one embodiment, the detector 28 is a gas chromatography type detector, such as a FID. Other embodiments of the detector 28 include, but are not limited to, a mass spectrometer and an evaporative light scattering detector. Other types of detectors can be used in connection with the embodiments of thermally modulated variable restrictors described herein.

The chromatography system 10 can also include one or more sensors 30 for measuring parameters such as system pressure, gradient composition, temperature of the mobile phase, and mass flow rate. The one or more sensors 30 can be disposed at various points in the mobile phase streams 16, 22-1, and 22-2. For illustration purposes, FIG. 1 shows a sensor 30 disposed between the separation column 18 and the tee fitting 21. This sensor 30 can be a pressure transducer that measures the system pressure before the stream of mobile phase 16 is split. Alternatively, this sensor 30 can be a viscometer configured to measure the composition of the mobile phase. Such measurements can be used to detect changes in the chromatographic run, for example, those pressure changes corresponding to a density program or mobile phase composition changes corresponding to a composition gradient. As another example, one sensor 30 disposed in the main mobile phase flow 16 can measure the total mass flow rate, and a second sensor 30 disposed in the minority mobile phase stream 22-2 can measure the mass flow rate of the minority portion. From the ratio of these flow rates, the split ratio can be determined.

A controller 32 is in communication with the solvent delivery system 12, the BPR 24 (connection to the BPR 24 not shown), the one or more sensors 30, and the thermally modulated variable restrictor 26. The controller 32 can run a density program by which the controller 32 controls the system pressure produced by the solvent delivery system 12 during the course of the chromatographic run, or run a gradient schedule by which controller 32 controls the mobile phase composition produced by the solvent delivery system 12.

In addition, the controller 32 reads the measured parameters from the one or more sensors 30. From these measurements, the controller 32 can detect when monitored parameters have changed and, in response, control the temperature setting of the variable restrictor 26 accordingly, in order to maintain a constant split ratio. For example, the controller 32 can be preprogrammed to map system pressures to temperatures of the variable restrictor 26. Further, the variable restrictor 26 is calibrated in the chromatography system 10 to produce a particular split ratio when the variable restrictor 26 is set to a given temperature. Feedback to the controller 32 from the sensor 30 provides the current condition of a monitored parameter (e.g., system pressure) of the chromatographic run. The controller 32 determines from the current value of the monitored parameter whether to change the temperature of the variable restrictor 26. If an adjustment to temperature is necessary to maintain the target split ratio, the controller 32 causes the variable restrictor 26 to heat or cool the second mobile phase stream 22-2 as the current condition warrants. It is to be understood that the various functions of the controller 32 can be distributed across more than one controller.

Figure 2:
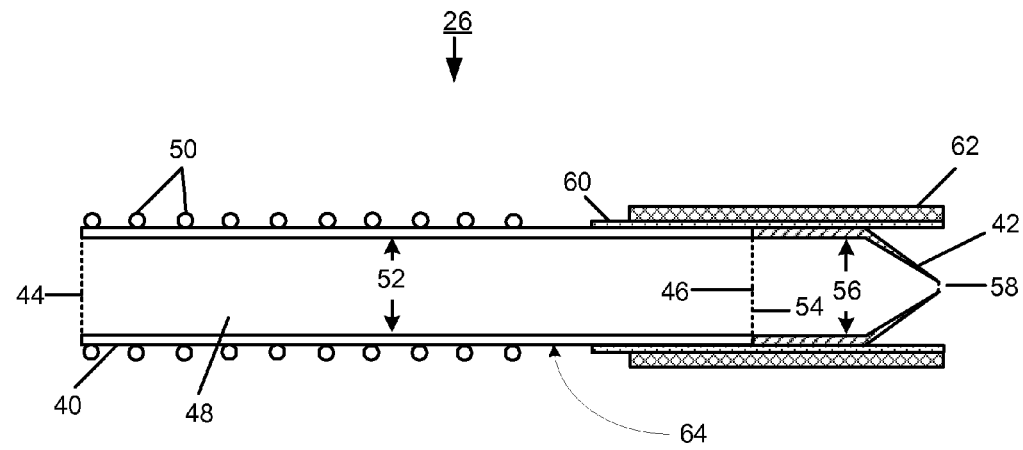
FIG. 2 is a cross-sectional view of one embodiment of the thermally modulated variable restrictor.

FIG. 2 shows an example embodiment of a thermally modulated variable restrictor 26 that can be employed in the chromatography system 10 of FIG. 1. The variable restrictor 26 comprises a restrictor body 40 (implemented as a tube) coupled to a tapered restrictor tip 42. The restrictor body 40 has an inlet end 44 (which couples directly to an outlet of the tee fitting 21 of FIG. 1), an outlet end 46, and a bore 48 extending therethrough that provides a fluidic channel for the mobile phase stream 22-2 flowing into the inlet end 44 from the tee fitting 21. In this embodiment, a heating element 50, for example, a Nichrome wire with a polyimide coating, coils around a short section of the restrictor body 40. The heating element 50 begins at the inlet end 44 of the restrictor body 40 and ends before reaching the restrictor tip 42, and the restrictor tip 42 is unheated. The restrictor tip 42 can be heated without departing from the principles described herein. Often, the restrictor tip 42 resides within a heated region of a detector (e.g., a flame ionization detector, evaporative light scattering, mass spectrometry). In such instances, the restrictor tip 42 is held at a constant temperature, typically greater than the temperature of the restrictor body 40. Notwithstanding, the heating of the restrictor tip 42 may have negligible effect on the split ratio because the linear velocity of the mobile phase stream 22-2 through the restrictor tip 42 is so great as to present little time for further energy transfer.

Compared to the tip orifice, the ID 52 of the bore 48 is relatively large so that the mass flow rate of the mobile phase through the restrictor body 40 is slow enough to facilitate energy transfer from the heating element 50 to the second mobile phase stream 22-2. The outlet end 46 of the restrictor body 40 abuts the inlet end 54 of the restrictor tip 42. The ID 56 of the restrictor tip 42 matches the ID 52 of the restrictor body 40 at the inlet end 54 and tapers to a narrow opening 58 smaller than the ID 52. This taper provides the restriction on the mobile phase flow 22-2.

A tubing connector, comprised of an intermediate tube 60 and an outer tube 62, is one example of an attachment mechanism for coupling the restrictor body 40 to the restrictor tip 42. The intermediate tube 60 surrounds the outlet end 46 of the restrictor body 40 and the restrictor tip 42; the outer tube 62 (preferably stainless steel) surrounds a majority portion of the intermediate tube 60. As such, the tubing connector protects the end 46 of the restrictor body 40. Annular crimps (not shown) can permanently affix the outer and intermediate tubes to each of the restrictor body 40 and restrictor tip 42. Examples of such annular crimps are described in U.S. application Ser. No. 14/233,212, filed Jan. 16, 2014., titled "Liquid Chromatography Conduit Assemblies having High Pressure Seals", the entirety of which application is incorporated by reference herein.

Other attachment mechanisms can be employed with departing from the principles described herein. For example, a union (not shown) can be used to connect the restrictor body 40 to the restrictor tip 42. Rather than join within the tubing connector, the union can join the restrictor body 40 to the restrictor tip 42 outside of the unheated zone, for example, at point 64. The connection can be non-destructively detachable, enabling the replacement of plugged restrictor tips, and prolonging the useful life of the restrictor body.

During a chromatography run, the mobile phase stream 22-2 received by the variable restrictor 26 from the tee fitting 21 preferably remains predominantly liquefied throughout its passage through the restrictor body 40. Because of the relative shortness of the heated section, the mobile phase does not decompress before reaching the restrictor tip 42. At the outlet 58 of the restrictor tip 42, the mobile phase transitions to gas and evaporates, leaving the analytes to be passed on to the detector 28 (FIG. 1). Advantageously, the analytes carried by the liquefied mobile phase tend not precipitate from the mobile phase within the restrictor body 40 (and, consequently, this tendency reduces the likelihood of plugging).

Figure 3:
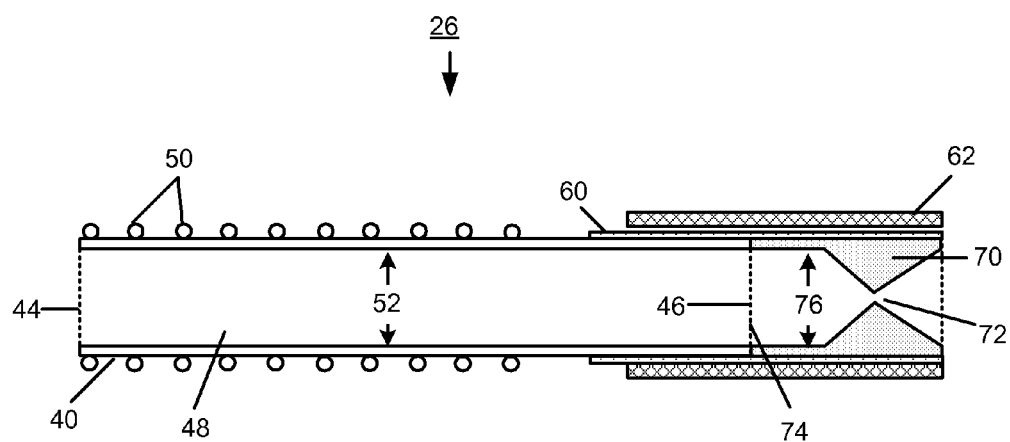
FIG. 3 is a cross-sectional view of another embodiment of the thermally modulated variable restrictor.

FIG. 3 shows another embodiment of the thermally modulated variable restrictor 26 having the restrictor body 40 of the FIG. 2 coupled to a pinched restrictor tip 70, also referred to as a converging-diverging restrictor. The outlet end 46 of the restrictor body 40 abuts the inlet end 74 of the restrictor tip 70. The ID 76 of the restrictor tip 70 matches the ID 52 of the restrictor body 40 at the inlet end 74, pinches to a narrow opening 72 smaller than the ID 52, and widens towards the outlet end of the restrictor tip 70. This pinch provides the restriction on the mobile phase flow. A laser process can produce the pinch in the restrictor tip 70 by decreasing the ID 76 from opposite ends of the tip 70 towards the narrow opening 72, while the dimension of the outer diameter (OD) of the restrictor tip 70 remains unchanged. The tubing connector described in connection with FIG. 2, for example, can couple the restrictor body 40 to the restrictor tip 70.

Figure 4:
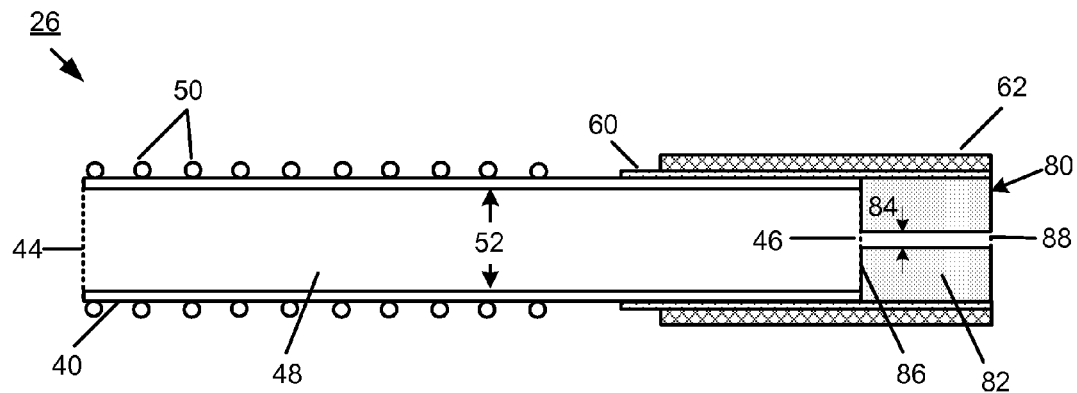
FIG. 4 is a cross-sectional view of another embodiment of the thermally modulated variable restrictor.

FIG. 4 shows yet another embodiment of the thermally modulated variable restrictor 26 having the restrictor body 40 of FIG. 2 coupled to a linear restrictor tip 80 comprised of a short section of tubing 82 having a smaller ID 84 than the ID 52 of the restrictor body 40. The outlet end 46 of the restrictor body 40 abuts the inlet end 86 of the restrictor tip 80. The outlet end of the restrictor tip 80 has a single narrow opening 88 (the size of the ID 84). The tubing connector described in connection with FIG. 2, for example, can couple the restrictor body 40 to the restrictor tip 80.

Figure 5:
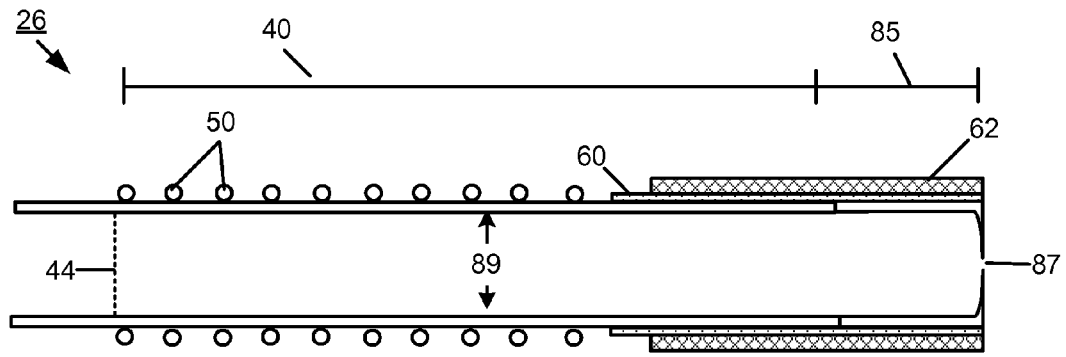
FIG. 5 is a cross-sectional view of another embodiment of the thermally modulated variable restrictor.

FIG. 5 shows still another embodiment of the thermally modulated variable restrictor 26 with the restrictor body 40 and an integral restrictor tip 85. The restrictor tip 85 is formed by melting the end of a fused silica capillary closed and sanding back the closed end until a small orifice 87 is formed. The orifice 87 has a smaller ID than the ID 89 of the restrictor body 40. The end of the restrictor tip 85 abuts the end of the restrictor body 40. Although this type of restrictor is called an integral restrictor, the restrictor tip 85 does not necessarily need to be integral to the heated region (i.e., the restrictor body).

Each of the restrictor tips 42, 70, 80, and 85 of FIG. 2, FIG. 3, FIG. 4, and FIG. 5, respectively, is relatively immune to plugging from analyte precipitation because of their short decompression distances. Each of such restrictor tips has a single narrow opening, which can be susceptible to plugging from a small solid particle that becomes lodged in the orifice. To overcome the susceptibility of a single narrow tip to plugging, each of the restrictor tips shown in FIG. 2, FIG. 3, or FIG. 5 can be packed with small (~1 to 5 um) silica particles. These particles can be, for example, sintered by laser in place within the tip to form a packed taper. Other examples of fixing the particles within the tip include, but are not limited to, forms of thermal sintering or polymeric fritting methods. In addition to packing with silica particles, methods of forming a frit within the restrictor tip include, but are not limited to, employing a porous polymer fixed in place, or a monolithic silica structure formed by using silicates. The packed taper allows for similar performance to that of the restrictor tips of FIG. 2, FIG. 3, or FIG. 5, but with less likelihood of plugging in the event of a single solid particulate.

Figure 6:
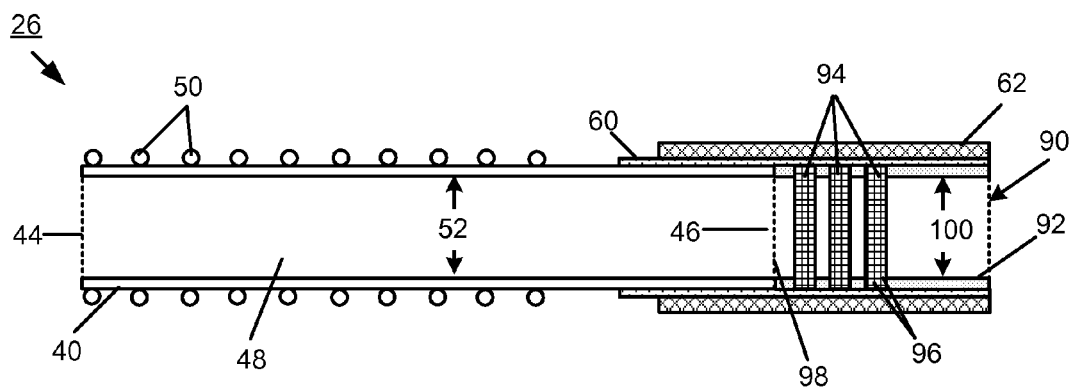
FIG. 6 is a cross-sectional view of another embodiment of the thermally modulated variable restrictor.

FIG. 6 shows an embodiment of a thermally modulated variable restrictor 26 that also overcomes the susceptibility of a single narrow opening. The thermally modulated variable restrictor 26 of FIG. 6 includes the restrictor body 40 of FIG. 2 coupled to a fritted restrictor tip 90. The restrictor tip 90 includes tubing 92 with one or more frits 94 packed therein. Each frit 94 in the tubing 92 is a porous element, made of stainless steel or other inert metal or plastic, having multiple small openings or pores 96 through which can pass the mobile phase with the sample. In other embodiments, a frit 94 can be formed using a continuous bed of, for example, sintered silica particles, silica particles bonded with polymer, entirely a porous polymer fixed in place, or a monolithic silica structure formed by using silicates.

Each pore 96 of a frit 94 provides a different decompression path for the mobile phase. Whereas any given pore of a frit 94 may become blocked by a small particle, the unlikelihood of every pore becoming blocked ensures that the restrictor tip 90 is effectively immune from plugging. The outlet end 46 of the restrictor body 40 abuts the inlet end 98 of the restrictor tip 90. The ID 100 of the restrictor tip 90 matches the ID 52 of the restrictor body 40. The tubing connector described in connection with FIG. 2, for example, can couple the restrictor body 40 to the restrictor tip 90.

Figure 7:
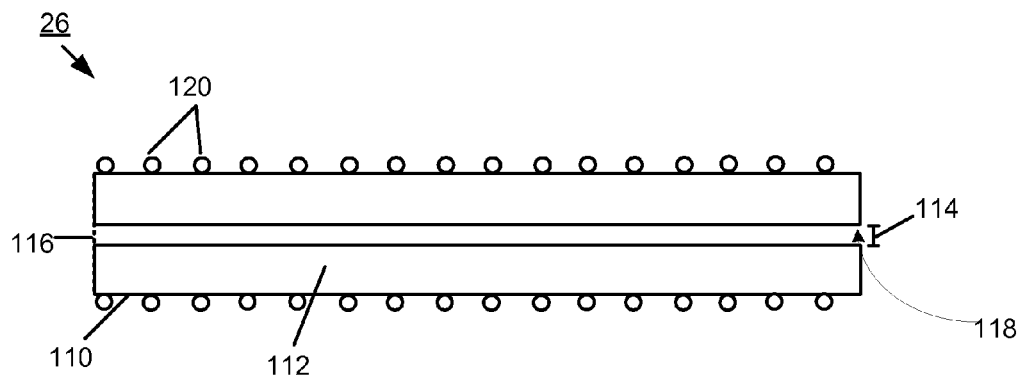
FIG. 7 is a cross-sectional view of another embodiment of the thermally modulated variable restrictor.

FIG. 7 shows still yet another embodiment of the thermally modulated variable restrictor 26 that can be used in the chromatography system 10 of FIG. 1 to keep the split ratio constant throughout a chromatographic run. This embodiment of the thermally modulated variable restrictor 26, which is a conventional linear heated restrictor, has a restrictor body 110 comprised of tubing 112 with a constant small ID 114 throughout the tubing 112 from the inlet end 116 to the outlet end 118. The thermally modulated variable restrictor 26 restricts the mobile phase flow 22-2 by having an ID 114 that is smaller than that of the separation column 18. A heating element 120 wraps around a majority portion of the length of the tubing 112.

Figure 8:
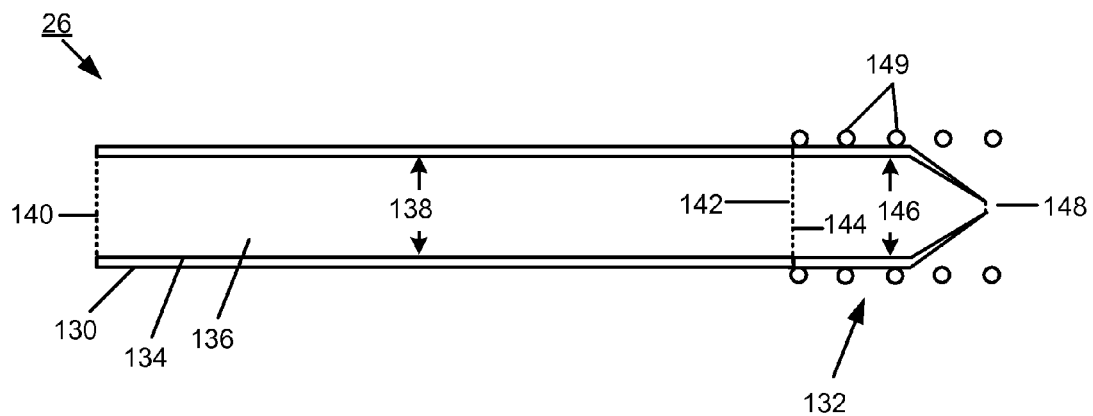
FIG. 8 is a cross-sectional view of another embodiment of the thermally modulated variable restrictor.

The thermally modulated variable restrictor 26 of FIG. 8 illustrates another embodiment that can be used in the chromatography system 10 of FIG. 1 to keep the split ratio constant throughout a chromatographic run. This conventional embodiment of a restrictor has a restrictor body 130 coupled to a heated tapered restrictor tip 132 (alternatively, the restrictor body 130 and restrictor tip 132 can be an integral unit). The restrictor body 130 comprises tubing 134 having a bore 136 with a relatively large ID 138 that extends from an inlet end 140 to an outlet end 142. The outlet end 142 of the restrictor body 130 abuts the inlet end 144 of the restrictor tip 132. The ID 146 of the restrictor tip 132 matches the ID 138 of the restrictor body 130 at the inlet end 142 and tapers to a narrow opening 148 smaller than the ID 146. This taper provides the restriction on the mobile phase flow 22-2.

The embodiment is similar in shape to that of the embodiment of FIG. 2, except that the heating element 149 is disposed at the tapered restrictor tip 132, to heat the mobile phase as it is about to exit the variable restrictor 26 through the outlet end 148. Because of the short distance within which to achieve a heat transfer to the mobile phase effective for purposes of controlling the split ratio, the temperature of the heating element 149 may need to range between 200° C. and 800° C. or even considerably higher (before reaching the softening point of fused silica, which is as high as 1700° C.).

Figure 9:
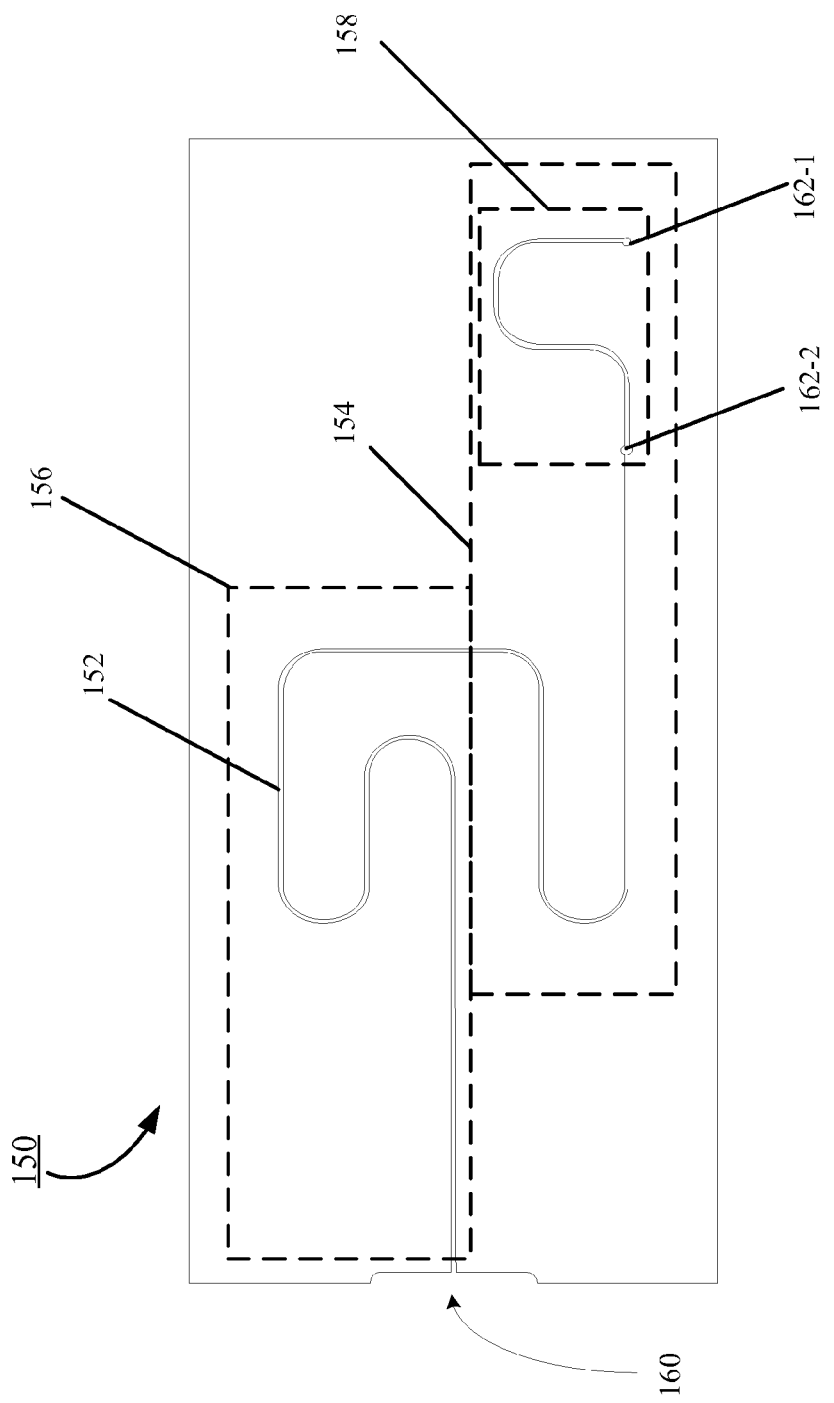
FIG. 9 is a top view of a microfluidic substrate (or tile) having a fluidic channel, a subsection of which embodies a restrictor body of a thermally modulated variable restrictor.

FIG. 9 shows an example of a microfluidic substrate (or tile) 150 that can be used to implement an embodiment of a restrictor body of a thermally modulate variable restrictor 26. The microfluidic substrate 150 is generally rectangular, flat, and thin (approx. 0.050") and has a multilayer construction. Example construction materials for the microfluidic substrate 150 include metallic (e.g., titanium, stainless steel), ceramic, glass, and polymeric. For protein samples, the microfluidic substrate 150 is preferably a High-Temperature Co-fired Ceramic (HTCC), which provides suitably low levels of loss of sample because of attachment of sample to walls of conduits in the substrate. Example implementations of microfluidic substrates are described in U.S. application Ser. No. 12/282,225, filed Mar. 19, 2007, titled "Ceramic-based Chromatography Apparatus and Methods for Making Same," the entirety of which is incorporated herein by reference. The microfluidic substrate 150 can be housed in a microfluidic cartridge, as described in U.S. application Ser. No. 13/202,354, filed Nov. 4, 2011, titled "Electrospray Interface to a Microfluidic Substrate," the entirety of which is incorporated herein by reference.

Formed within the layers of the microfluidic substrate 150 is a serpentine fluidic channel 152 for transporting the mobile phase. The fluidic channel 152 can be, for example, lasered, etched, embossed, or machined into the substrate layers. The fluidic channel 152 passes through two regions of the microfluidic substrate 150, including a column region 154 and a restrictor body region 156. The column region 154 can include a trap region 158. Apertures 162-1 and 162-2 open into the fluidic channel 152 at opposite ends of the trap region 158. The fluidic aperture 162-2 at the "downstream" end of the trap region 158 is optionally used as a fluidic outlet aperture, for example, during loading of the trap region 158, and is optionally closed to fluid flow, for example, during injection of a loaded sample from the trap region 158 into the fluidic channel 152.

The fluidic channel 152 terminates at an opening 160 in an edge of the microfluidic substrate 150. A restrictor tip, such as any of those described in connection with FIG. 2, FIG. 3, FIG. 4, FIG. 5, and FIG. 6, can be brought into fluidic communication with this opening 160 to restrict the flow of the mobile phase 22-2 flowing through the fluidic channel 152. Techniques for interfacing a restrictor tip to an opening at the edge of a microfluidic substrate 150 are described in the aforementioned U.S. application Ser. No. 13/202,354. Alternatively, the fluidic channel 152 can terminate at an opening in a side of the substrate 150. Other types of restrictor tips can be integral to the microfluidic substrate, for example, a frit can be embedded into the microfluidic substrate at the egress end of the fluidic channel 152, or the opening 160 can be fashioned to be smaller than the ID of the fluidic channel 152. In contrast to the externally attached restrictor tips, the integral restrictors cannot be removed and replaced.

The sizes of the regions 154, 156, 158, and the shape and length of the fluidic channel 152 within each region, are merely illustrative examples. Other embodiments of microfluidic platforms 150 can have the restrictor body region 156 and column region 154 on different interconnected tiles, similar to that illustrated in the aforementioned U.S. application Ser. No. 13/202,354. In addition, the restrictor body and column regions 154, 156, whether implemented on the same or on different substrates, can be two independently controlled thermal regions.

Figure 10:
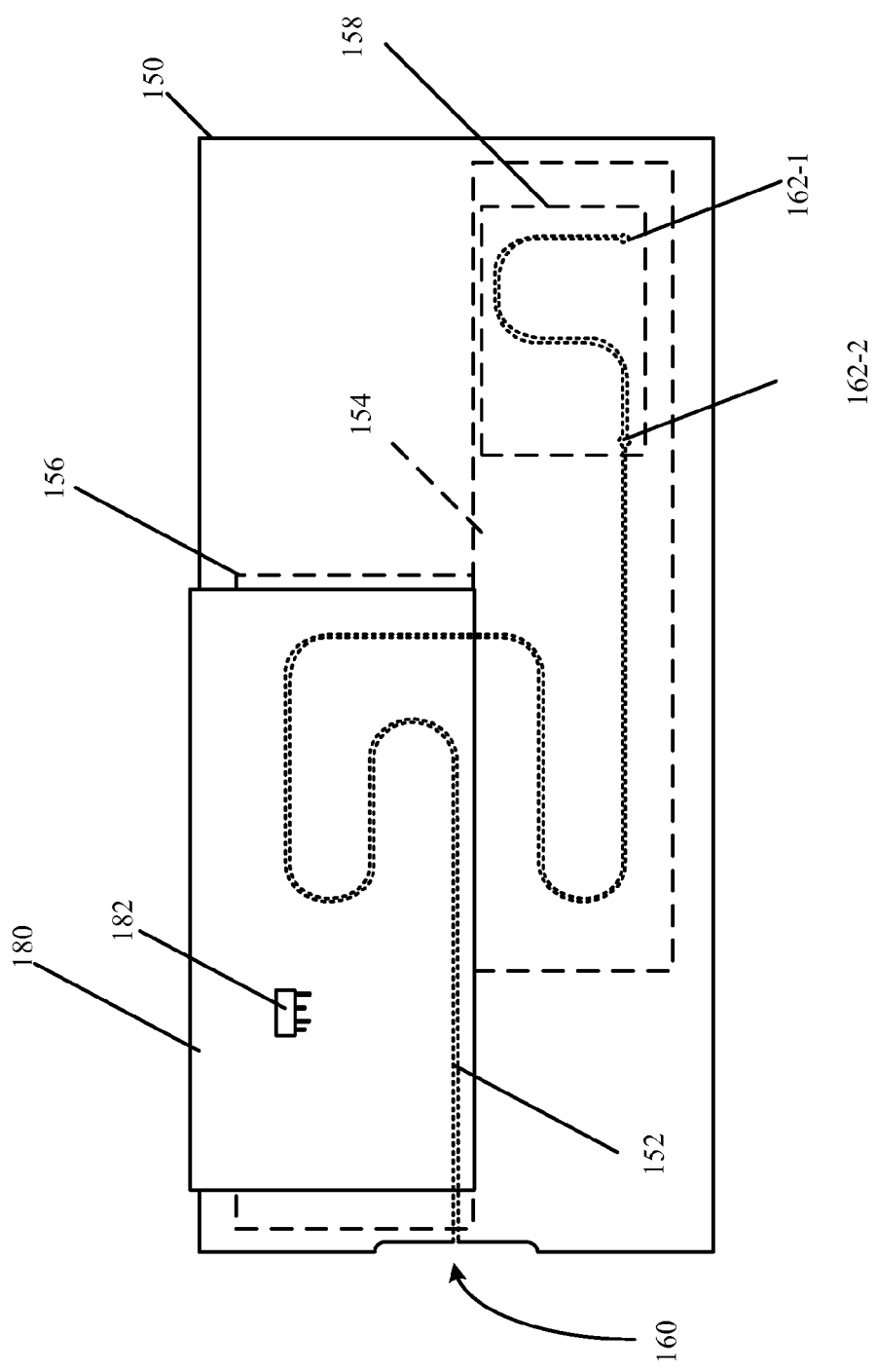
FIG. 10 is a top view of the microfluidic substrate with a heater disposed on a surface thereof to heat a subsection of the fluidic channel within the microfluidic substrate.

FIG. 10 shows an embodiment of a microfluidic substrate 150 with a flex circuit heater assembly 180 disposed on a side surface of the substrate 150. The multi-layer flex circuit heater assembly 180 covers the restrictor body region 156 of FIG. 9. A portion of the flex circuit heater assembly 180 can fold over the edge on onto the opposite side of the microfluidic substrate 150.

Immediately below the surface covered by the flex circuit heater assembly 180 is the region 156 of the fluidic channel 152 corresponding to the restrictive body. One layer of the flex circuit heater assembly 180 includes resistive traces that generate heat upon the passage of electrical current. The heat passes through the surface of the substrate 150 into the mobile phase 22-2 flowing through the fluidic channel 152 within the restrictor body region 156. Mounted to the flex circuit heater assembly 180 can be a temperature sensor 182 to measure the applied temperature. Another heater (not shown) can cover and independently control the temperature of the separation column region 154. In another embodiment, the heating of the restrictor body region 156 can be achieved using a deposited layer of ferromagnetic material and an inductive heater.

Figure 11:
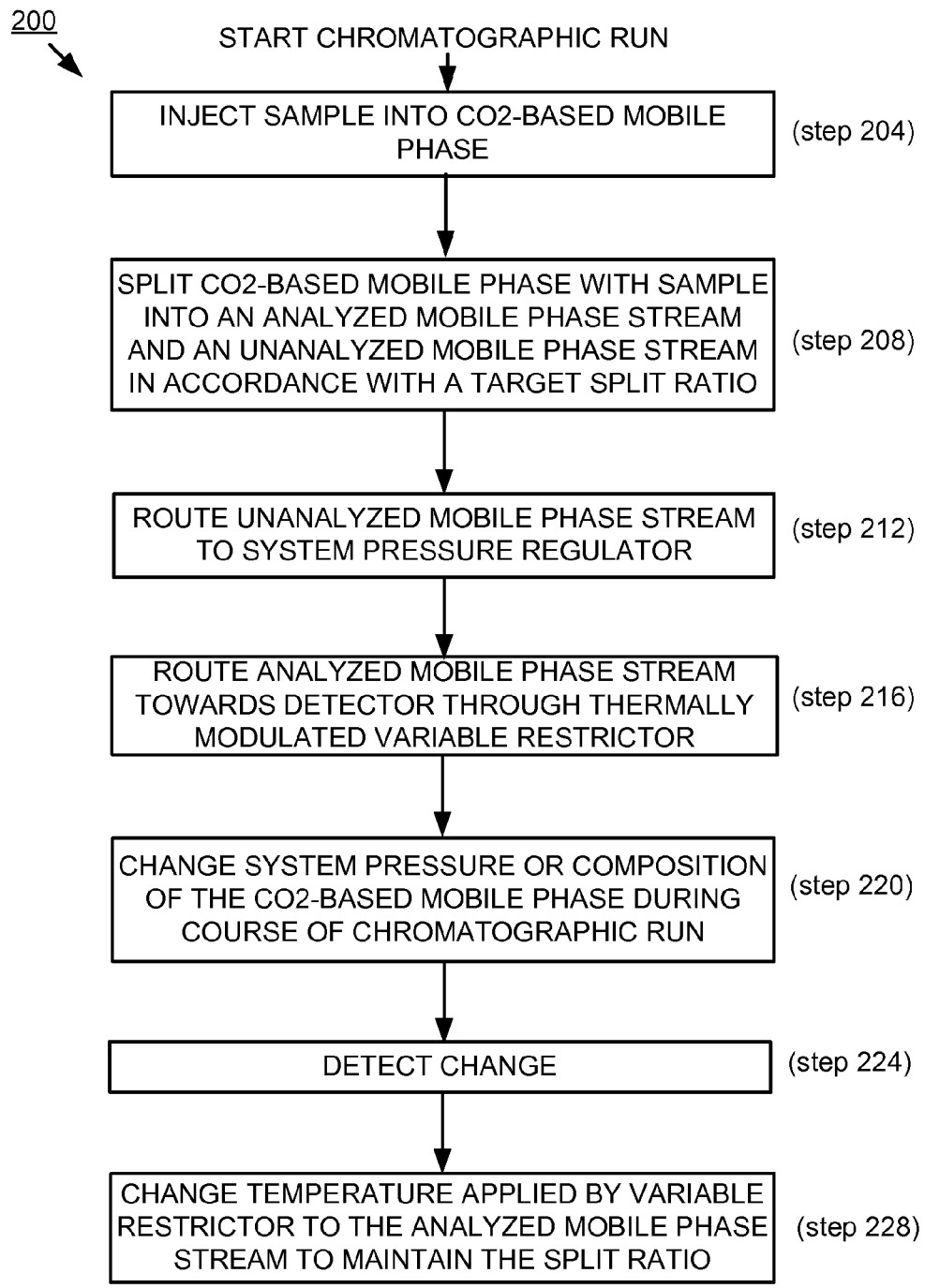
FIG. 11 is a flow diagram of an embodiment of a process for performing a chromatographic run.

FIG. 11 shows an embodiment of a process 200 for performing a chromatographic run during which the chromatography system 10 of FIG. 1 separates a sample into its constituents. In this description of the process 200, reference is made to various components of the chromatography system 10 of FIG. 1. At step 204, the sample injector 14 injects a sample into a $CO_2$-based mobile phase 16 pumped by the solvent delivery system 12. The mobile phase 16 with the sample passes through the separation column 18. The active splitter 20 splits (step 208) the $CO_2$-based mobile phase 16 with the sample into an unanalyzed mobile phase stream 22-1 and an analyzed mobile phase stream 22-2 in accordance with a target split ratio. The active splitter 20 routes (step 212) the unanalyzed mobile phase stream 22-1 to the system pressure regulator 24, and the analyzed mobile phase stream 22-2 (step 216) towards the detector 28 through the thermally modulated variable restrictor 26.

At step 220, the controller 32 changes the system pressure (or the gradient composition of the mobile phase 16) during the course of the chromatographic run in accordance with preprogrammed settings (e.g., a density program). The sensor 30 continuously measures a pertinent parameter (e.g., system pressure or the mobile phase composition) and provides the measurements to the controller 32. In response to these measurements, the controller 32 may detect (step 224) a change and use a new measurement to determine a new temperature setting for the variable restrictor 26. This new temperature setting is calibrated to cause the variable restrictor 26 to compensate for the change in a manner that keeps the split ratio constant despite the change. By raising or lowering the temperature provided by the variable restrictor 26, the temperature of the analyzed mobile phase stream 22-2 passing through correspondingly heats or cools. This change in the temperature of the analyzed mobile phase stream 22-2 causes a corresponding change in the degree of restriction produced by the variable restrictor 26. The resulting mass flow rate through the variable restrictor 26 attained by this new temperature setting operates to maintain the split ratio at its previously established target.

As will be appreciated by one skilled in the art, some aspects described herein may be embodied as a system, method, and computer program product. Thus, such aspects may be embodied entirely in hardware, entirely in software (including, but not limited to, firmware, program code, resident software, microcode), or in a combination of hardware and software. All such embodiments may generally be referred to herein as a circuit, a module, or a system.

In addition, some aspects may be in the form of a computer program product embodied in one or more computer readable media having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wired, optical fiber cable, radio frequency (RF), etc. or any suitable combination thereof.

Computer program code for carrying out operations for some described aspects may be written in any combination of one or more programming languages, including an object oriented programming language such as JAVA, Smalltalk, C#, C++, and Visual C++ or the like and conventional procedural programming languages, such as the C and Pascal programming languages or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may execute entirely on a user's computer, partly on the user's computer, as a stand-alone software package, partly on the user's computer and partly on a remote computer or entirely on a remote computer or server. Any such remote computer may be connected to the user's computer through any type of network, including a local area network (LAN) or a wide area network (WAN), or the connection may be made to an external computer (for example, through the Internet using an Internet Service Provider).

Some aspects are described with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments described herein. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for describing particular embodiments only and is not intended to be limiting of the invention. As used herein, the singular forms "a", "an" and "the" are intended to include the plural forms as well, unless the context clearly indicates otherwise. It is be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The description has been presented for purposes of illustration and description, but is not intended to be exhaustive or limited to the embodiments in the form disclosed. The embodiments described were chosen to explain the principles and their practical application, and to enable the understanding of others of ordinary skill in the art. Many modifications and variations will be apparent to those of ordinary skill in the art without departing from the principles described.

What is claimed is:

1. A chromatography system comprising:
    a separation column separating a sample carried by a compressible mobile phase flow into analytes;
    a fluidic splitter in fluidic communication with the separation column to receive and divide the compressible mobile phase flow containing the separated sample into first and second mobile phase streams in accordance with a split ratio;
    a thermally modulated variable restrictor coupled between the fluidic splitter and a detector, the thermally modulated variable restrictor receiving the first mobile phase stream from the fluidic splitter, the thermally modulated variable restrictor having a temperature element in thermal communication with the first mobile phase stream to exchange heat therewith; and
    a controller in communication with the thermally modulated variable restrictor, the controller dynamically adjusting a temperature setting of the temperature element of the thermally modulated variable restrictor to adjust the heat exchange between the thermally modulated variable restrictor and the first mobile phase stream in order to keep the split ratio constant throughout a chromatographic run.

2. The chromatography system of claim 1, further comprising a system pressure regulator coupled to the fluidic splitter to receive the second mobile phase stream and to control therewith a system pressure of the chromatography system.

3. The chromatography system of claim 1, wherein the separation column is an analytical-scale packed-bed separation column.

4. The chromatography system of claim 1, further comprising a sensor disposed in a path of the compressible mobile phase flow downstream of the separation column for measuring a parameter of the chromatographic run, and
    wherein the controller adjusts the temperature setting of the temperature element of the thermally modulated variable restrictor in response to detecting a change in the measured parameter.

5. The chromatography system of claim 4, wherein the sensor is a pressure transducer for measuring system pressure.

6. The chromatography system of claim 4, wherein the sensor is a composition sensor for measuring a composition of the compressible mobile phase flow.

7. The chromatography system of claim 1, wherein the temperature element of the thermally modulated variable restrictor is a heating element.

8. The chromatography system of claim 1, wherein the temperature element of the thermally modulated variable restrictor is a cooling element.

9. The chromatography system of claim 1, wherein the system pressure regulator is any one of a backpressure regulator (BPR), a fixed restrictor, and a thermally modulated variable restrictor.

10. The chromatography system of claim 1, wherein the thermally modulated variable restrictor comprises:
    a restrictor body having a fluidic channel with an inlet end that receives the first mobile phase stream from the splitter and an outlet end through which the first mobile phase stream leaves the fluidic channel, the restrictor body being thermally coupled to the temperature element for exchanging heat with the first mobile phase stream flow passing through the fluidic channel; and
    a restrictor tip disposed adjacent to the restrictor body at the outlet end of the fluidic channel.

11. The chromatography system of claim 10, wherein the restrictor tip has an egress opening that is smaller than an internal diameter of the fluidic channel.

12. The chromatography system of claim 10, wherein the temperature element is thermally coupled to a subsection of the fluidic channel between the inlet and outlet ends of the restrictor body.

13. The chromatography system of claim 10, wherein the restrictor body comprises a microfluidic substrate within which the fluidic channel is formed.

14. The chromatography system of claim 13, wherein the temperature element includes a circuit disposed on a surface of the microfluidic substrate to heat the first mobile phase stream flow passing through the fluidic channel.

15. The chromatography system of claim 14, wherein the temperature element includes an induction heater and a layer of ferromagnetic material deposited on the microfluidic substrate adjacent to the fluidic channel to heat the first mobile phase stream passing through the fluidic channel using inductive heating.

16. The chromatography system of claim 10, further comprising a fluidic connector joining the restrictor body to the restrictor tip, the fluidic connector comprising a tube crimped annularly about the restrictor tip.

17. The chromatography system of claim 16, wherein the restrictor tip is nondestructively detachable from the restrictor body.

18. The chromatography system of claim 10, wherein the restrictor tip is unheated.

19. The chromatography system of claim 10, wherein the restrictor tip comprises a converging-diverging restrictor.

20. The chromatography system of claim 10, wherein the restrictor tip has a tapered region that tapers to the egress opening.

21. The chromatography system of claim 10, wherein the restrictor tip has a frit within the egress opening.

22. The chromatography system of claim 10, wherein the restrictor tip includes a straight section with an internal diameter that is smaller than the internal diameter of the fluidic channel.

23. The chromatography system of claim 10, wherein the restrictor tip is an integral restrictor.

24. The chromatography system of claim 10, wherein the compressible mobile phase flow comprises carbon dioxide.

25. The chromatography system of claim 24, wherein the compressible mobile phase flow further comprises a modifier, a ternary additive, or a combination of one or more modifiers and one or more ternary additives.

26. The chromatography system of claim 10, wherein the temperature element heats the fluidic channel to a temperature ranging between ambient temperature and approximately 500° C.

27. The chromatography system of claim 10, wherein the internal diameter of the fluidic channel is less than 1 mm.

28. A method for performing a chromatographic run, the method comprising:
dividing a compressible mobile phase flow containing a separated sample in accordance with a split ratio whereby a first portion of the divided compressible mobile phase flow moves at a first mass flow rate towards a detector through a thermally modulated variable restrictor and a second portion of the divided compressible mobile phase flow moves at a second mass flow rate to a system pressure regulator; and
dynamically adjusting a temperature setting of the thermally modulated variable restrictor to adjust a heat exchange between the thermally modulated variable restrictor and the first portion of the divided compressible mobile phase flow in order to keep the split ratio constant throughout the chromatographic run.

29. The method of claim 28, further comprising:
measuring a parameter of the chromatographic run in a path upstream from where the compressible mobile phase flow is divided; and
detecting a change in the measured parameter, and
wherein the dynamically adjusting the temperature of the thermally modulated variable restrictor occurs in response detecting the change in the measured parameter.

30. The method of claim 29, further comprising changing a system pressure during the chromatographic run, wherein the measured parameter includes the system pressure.

31. The method of claim 29, further comprising changing a gradient composition of the compressible mobile phase flow during the chromatographic run, and wherein the measured parameter includes the gradient composition.

32. The method of claim 29, further comprising heating the first portion of the divided compressible mobile phase flow according to the dynamically adjusted temperature setting of the thermally modulated variable restrictor.

33. The method of claim 29, further comprising cooling the first portion of the divided compressible mobile phase flow according to the dynamically adjusted temperature setting of the thermally modulated variable restrictor.

34. The method of claim 28, further comprising regulating, by the system pressure regulator, system pressure using the second portion of the divided compressible mobile phase flow.

35. The method of claim 28, wherein the compressible mobile phase flow comprises carbon dioxide.

36. The method of claim 35, wherein the compressible mobile phase flow further comprises a modifier, a ternary additive, or a combination of one or more modifiers and one or more ternary additives.

* * * * *